(12) United States Patent
Wintch et al.

(10) Patent No.: US 11,193,599 B2
(45) Date of Patent: Dec. 7, 2021

(54) FLOWMETER BI-VALVE

(71) Applicant: Oxyswitch, LLC, Hurricane, UT (US)

(72) Inventors: Majere T. Wintch, Washington, UT (US); Wayne A. Provost, St. George, UT (US); Russell W. Jaramillo, Santa Clara, UT (US)

(73) Assignee: OXYSWITCH, LLC, Hurricane, UT (US)

( * ) Notice: Subject to any disclaimer, the term of this patent is extended or adjusted under 35 U.S.C. 154(b) by 0 days.

(21) Appl. No.: 17/093,805

(22) Filed: Nov. 10, 2020

(65) Prior Publication Data

US 2021/0054944 A1 Feb. 25, 2021

Related U.S. Application Data

(63) Continuation-in-part of application No. PCT/US2019/028717, filed on Apr. 23, 2019, which
(Continued)

(51) Int. Cl.
| | |
|---|---|
| *F16K 11/087* | (2006.01) |
| *A61M 16/20* | (2006.01) |
| *A61M 16/00* | (2006.01) |

(52) U.S. Cl.
CPC ....... *F16K 11/0873* (2013.01); *A61M 16/201* (2014.02); *A61M 2016/003* (2013.01);
(Continued)

(58) Field of Classification Search
CPC .. F16K 11/0873; F16K 11/056; F16K 11/087; A61M 16/201; A61M 2016/003; A61M 2202/0208; A61M 2202/0275
See application file for complete search history.

(56) References Cited

U.S. PATENT DOCUMENTS 3,057,370 A * 10/1962 Hamilton .............. F16K 27/062
137/315.09
3,334,658 A 8/1967 Kaatz
(Continued)

FOREIGN PATENT DOCUMENTS

| CN | 202263277 U | 6/2012 |
| CN | 103520818 A | 1/2014 |

(Continued)

OTHER PUBLICATIONS

"Flow Selector" Precision Medical, accessed Sep. 13, 2018; URL: http://www.precisionmedical.com/hospitals/specialty-products/flow-selector.
(Continued)

*Primary Examiner* — Kendra D Carter
*Assistant Examiner* — Jonathan S Paciorek
(74) *Attorney, Agent, or Firm* — Workman Nydegger

(57) ABSTRACT

The present disclosure describes a bi-valve for use with a flowmeter or other source of oxygen or other medical gas, that allows a medical practitioner to easily and quickly switch from delivering oxygen or other gas from the flowmeter or other gas source to a given mask or other device, to another mask or other device. This is accomplished far faster and easier than is done under current practice. Current practice results in the patient being off oxygen or other gas for a short, but very significant period of time, which poses a serious risk of desaturation in the patient. The bi-valve may include a casing, an inlet, and two outlets, with a knob for selecting which output the oxygen or other gas is to be delivered to. The device may be a very simple ball valve device, with the only moving parts being the knob and the ball.

18 Claims, 8 Drawing Sheets

Related U.S. Application Data is a continuation-in-part of application No. 16/134,753, filed on Sep. 18, 2018, now abandoned.

(60) Provisional application No. 62/670,092, filed on May 11, 2018.

(52) U.S. Cl.
CPC .............. *A61M 2202/0208* (2013.01); *A61M 2202/0275* (2013.01)

(56) References Cited

U.S. PATENT DOCUMENTS

| | | | |
|---|---|---|---|
| 3,943,971 A * | 3/1976 | Schmunk | F16K 11/00 137/872 |
| 4,576,234 A * | 3/1986 | Upchurch | E21B 34/103 166/319 |
| 4,628,749 A | 12/1986 | Rafter, Jr. | |
| D395,500 S | 6/1998 | Ryder | |
| 5,857,663 A | 1/1999 | Evans et al. | |
| 5,944,055 A * | 8/1999 | Dicky | F16K 11/0873 137/625.47 |
| 5,988,220 A | 11/1999 | Sakaki | |
| 6,622,933 B1 | 9/2003 | Young et al. | |
| 6,779,560 B1 | 8/2004 | Reis | |
| 7,255,131 B2 | 8/2007 | Paper et al. | |
| 7,409,966 B2 * | 8/2008 | Chang | F16K 5/0642 137/625.47 |
| 7,849,877 B2 | 12/2010 | Tan et al. | |
| D634,420 S | 3/2011 | Hanada et al. | |
| D634,813 S | 3/2011 | Hernandez, IV | |
| 8,770,227 B2 | 7/2014 | Hernandez, IV et al. | |
| D724,181 S | 3/2015 | Condon et al. | |
| D845,438 S | 4/2019 | Wintch et al. | |
| 2005/0229934 A1 | 10/2005 | Willeford | |
| 2006/0169337 A1 | 8/2006 | Lopez | |
| 2007/0062590 A1 | 3/2007 | Paper et al. | |
| 2008/0000472 A1 * | 1/2008 | Wall | A61M 16/20 128/202.27 |
| 2008/0210309 A1 | 9/2008 | Tan et al. | |
| 2009/0236000 A1 | 9/2009 | Miller et al. | |
| 2010/0126598 A1 | 5/2010 | Peric et al. | |
| 2010/0174210 A1 * | 7/2010 | Han | A61B 10/0096 600/581 |
| 2019/0344040 A1 | 11/2019 | Wintch et al. | |

FOREIGN PATENT DOCUMENTS

| | | |
|---|---|---|
| CN | 103877657 A | 6/2014 |
| WO | 2019/217068 A1 | 11/2019 |

OTHER PUBLICATIONS https://www.wtfarley.com/Flow-Selector-Valve?gclid=Cj0KCQiA5bz-BRD-ARIsABJT4nhNGTdcURntfpWmolaKFPrIF-3y3fVur22GgPV4EsoJt7gaZnf7b00aApawEALw_wcB, accessed Dec. 8, 2020.

Instrumentation Industries, Inc., Oxygen (O2) Delivery Accessories, accessed Sep. 13, 2018; URL: https://www.iiimedical.com/proddetail.php?prod=SC603-A.

International Preliminary Reporton Patentability received for PCT Patent Application No. PCT/US2019/028717, dated Nov. 26, 2020, 6 pages.

International Search Report and Written Opinion received for PCT Patent Application No. PCT/US2019/028717, dated Aug. 19, 2019, 7 pages.

Notice of Allowance received for U.S. Appl. No. 29/664,347, dated Jan. 28, 2019.

U.S. Appl. No. 16/134,753, filed May 8, 2019, Final Office Action.

U.S. Appl. No. 16/134,753, filed Jan. 14, 2019, Office Action.

\* cited by examiner

FLOWMETER BI-VALVE

CROSS-REFERENCE TO RELATED APPLICATIONS

This application is a continuation-in-part of PCT Patent Application No. PCT/US2019/028717, filed Apr. 23, 2019, which claims the benefit of U.S. patent application Ser. No. 16/134,753 filed Sep. 18, 2018, and 62/670,092, filed May 11, 2018, each of which is herein incorporated by reference in its entirety.

BACKGROUND OF THE INVENTION

1. The Field of the Invention

The present invention is in the field of valves for use with medical equipment. More particularly, the invention relates to a bi-valve for use with a flowmeter.

2. The Relevant Technology

In a hospital setting, many patients receive medical gas, whether it's oxygen, medical grade air, nitric oxide, heliox, or other gas. As such, flowmeters are necessary and are usually found in each room of a hospital. Some patients need a constant flow of oxygen and are unable to maintain their saturation above 90% when off of the oxygen for any significant amount of time. Nonetheless, these patients are often removed from oxygen for one reason or another, even if it is just to switch to a different mask, cannula or other device (e.g., nebulizer, EzPAP®, TheraPEP®, etc.). Removing the patient from oxygen poses a serious health risk, and is a stressful occurrence for the nurses and respiratory therapists. Even when changed quickly, the patient's saturation could drop drastically, having health consequences.

Contributing to the time delay in switching a patient from one device to another is the entanglement of tubes. In other words, with several options hanging in the same general location, it may take time to sort out the tubes, figuring out what is what. Accordingly, there remains a need for a device and method of switching between gases and devices that lowers the risk of desaturation to the patient. It would be particularly beneficial if such device were simple, inexpensive and disposable rather than complex and not particularly suited to the purpose, such as is the case with CN202263277U, CN103877657A, and CN103520818A. For example, such devices are not simple, nor disposable, and are configured for different purposes, e.g., to deliver nebulizer treatment without disconnecting a humidifier.

SUMMARY

In one aspect, the present invention is directed to a bi-valve device, e.g., for use with a flowmeter that meters oxygen or other medical gas. It will be appreciated that such a bi-valve device may be used in conjunction with various other sources of medical gas, e.g., such as oxygen tanks or other sources of medical gas. The device may be particularly helpful for patient transfer from one location to another, e.g., from the operating room to intensive care, or long term facilities providing needed options for life saving events, in air-med or land-based ambulance transport where weight and space may be at a premium, etc. Other situations and environments for use will be apparent to those of skill in the art, in light of the present disclosure.

The device allows for quicker and better outcomes for the patient in need. The bi-valve device includes a casing, an inlet (e.g., a single inlet) into which oxygen or other medical gas is introduced from a flowmeter or other source to the casing, and dual outlets through which oxygen or other medical gas can be selectively output from the casing. The bi-valve further includes a knob attached to (e.g., partially contained within) the casing that is configured to selectively direct flow of oxygen or other medical gas from the inlet into a selected one of the dual outlets. In an embodiment, the bi-valve includes two and only two outlets. For example, while three or more outlets could be provided, Applicant has found that such dramatically increases the potential for human error that could result in harm to the patient. Such also increases the cost and complexity of the device.

More specifically, an embodiment of the bi-valve device may include a two-piece casing including an upper piece and a lower piece (e.g., two initially separate pieces that are glued or otherwise attached together during assembly). A single inlet is provided which permits oxygen or other gas from the flowmeter or other source to be introduced into the casing of the bi-valve. Dual outlets are provided through which oxygen can be selectively output from the casing. A 3-port ball may be provided in the casing, which is selectively rotatable within the casing, by rotating the knob. For example, the knob may include a base (positioned in the casing) and an elongate handle portion (positioned out of the casing). The base may be permanently matingly received in the ball (e.g., non-removable). The elongate handle portion of the knob is rotatable from (i) a first position in which oxygen flow into the inlet is directed to the first outlet to (ii) a second position in which oxygen flow into the inlet is directed to the second outlet. The knob, ball, and outlets may be configured and aligned so that the longitudinal axis of the rotatable elongate handle portion is aligned with the first outlet when in the first position, and the longitudinal axis of the rotatable elongate handle portion is aligned with the second outlet when in the second position.

The device can be manufactured very simply, e.g., so that the knob and the 3-port ball are the only moving parts of the device. For example, the device may include no internal springs, discs, levers, or other internal mechanical features that move. Because of its simplicity, the device can be manufactured inexpensively, so as to be disposable, e.g., after use(s) with a single patient, or after a single use. Such disposability and low cost decrease risk of cross-contamination from one patient to another as a result of re-use, that might otherwise occur.

The bi-valve device allows two masks, a mask and cannula device, mask or bag, or any other two devices to be simultaneously connected to the flowmeter, with a practitioner able to quickly and easily switch from one to the other by simply rotating the knob of the bi-valve. This can be done quickly and easily, minimizing risk of desaturation in a given patient. For example, such methods allow a practitioner to switch a patient from one attached mask, cannula, bag or other device to another mask, cannula, bag or other device in a matter of seconds (e.g., within 10 seconds, within 5 seconds, within 3 seconds, etc.). Such very quick switching from one mask or other device to the other minimizes risk of desaturation in the patient. For example, under existing procedures commonly used in a health-care setting, 2 to 5 minutes can often be spent with a patient removed from oxygen or other medical gas. While seemingly brief, such periods are easily sufficient for some patients to experience serious desaturation. Such desaturation of the patient from oxygen or other medical gas can have serious consequences.

The present device and method greatly reduces the amount of time that a patient may be removed from such gas during switching, e.g., to less than 1 minute, less than 30 seconds, or less than 10 seconds.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The drawings illustrate several embodiments of the invention, wherein identical reference numerals refer to identical or similar elements or features in different views or embodiments shown in the drawings.

DETAILED DESCRIPTION OF THE PREFERRED EMBODIMENTS

I. Definitions

Figure 1:
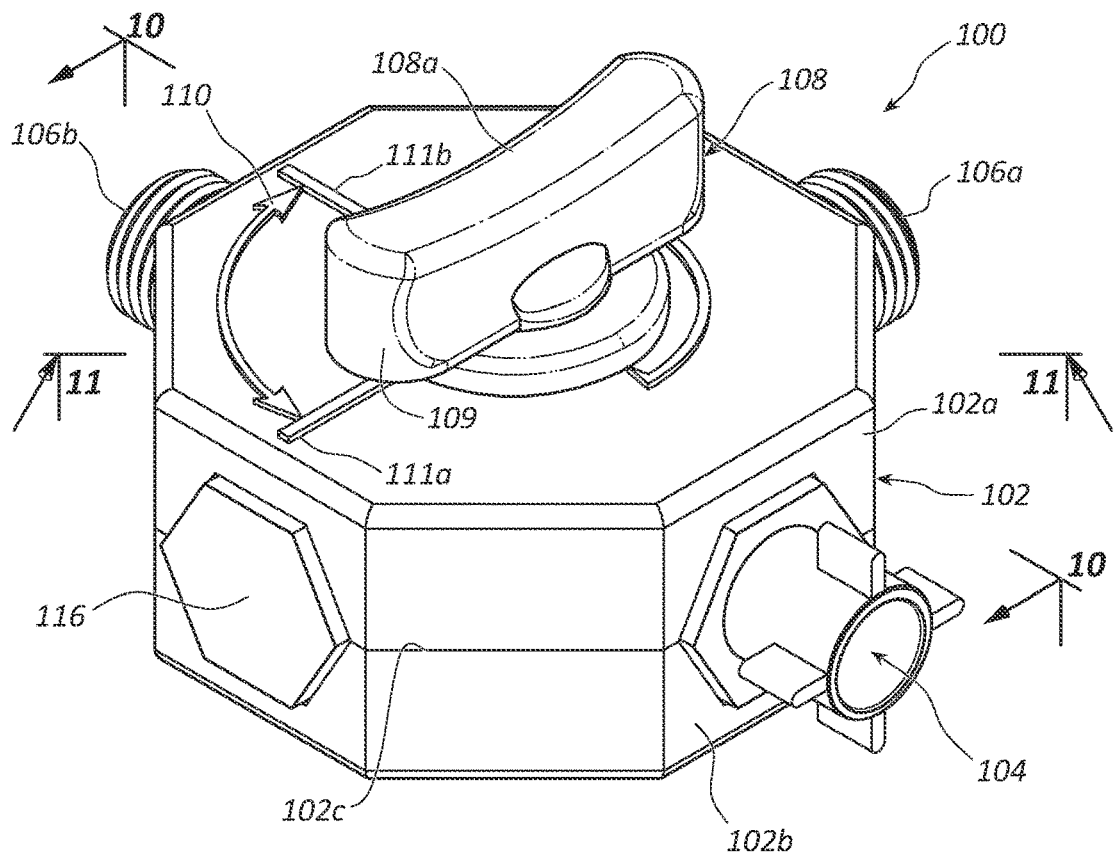
FIG. 1 is a top perspective view of an exemplary bi-valve device.

Some ranges may be disclosed herein. Additional ranges may be defined between any values disclosed herein as being exemplary of a particular parameter. All such ranges are contemplated and within the scope of the present disclosure.

Numbers, percentages, ratios, or other values stated herein may include that value, and also other values that are about or approximately the stated value, as would be appreciated by one of ordinary skill in the art. A stated value should therefore be interpreted broadly enough to encompass values that are at least close enough to the stated value to perform a desired function or achieve a desired result, and/or values that round to the stated value. The stated values include at least the variation to be expected in a typical manufacturing process, and may include values that are within 10%, within 5%, within 1%, etc. of a stated value. Furthermore, the terms "substantially", "similarly", "about" or "approximately" as used herein represent an amount or state close to the stated amount or state that still performs a desired function or achieves a desired result. For example, the term "substantially" "about" or "approximately" may refer to an amount that is within 10% of, within 5% of, or within 1% of, a stated amount or value.

All numbers used in the specification and claims are to be understood as being modified in all instances by the term "about", unless otherwise indicated. Notwithstanding that the numerical ranges and parameters setting forth the broad scope of the subject matter presented herein are approximations, the numerical values set forth in the specific examples are reported as precisely as possible. Any numerical value, however, inherently contains certain errors necessarily resulting from the standard deviation found in their respective testing measurements.

It must be noted that, as used in this specification and the appended claims, the singular forms "a," "an" and "the" include plural referents unless the content clearly dictates otherwise.

All publications, patents and patent applications cited herein, whether supra or infra, are hereby incorporated by reference in their entirety to the same extent as if each individual publication, patent or patent application was specifically and individually indicated to be incorporated by reference.

II. Introduction

In one embodiment, the present invention is directed to a bi-valve device for use with a flowmeter or other source of oxygen or other medical grade gas supply (e.g., medical grade air, nitric oxide, heliox or the like). The bi-valve allows a practitioner to easily and quickly switch from providing such gas to one face mask, cannula, bag, cannula bag, nebulizer or other patient device to another, on the fly, quickly, in a manner that minimizes risk of desaturation of the gas in the patient. The bi-valve includes a casing, an inlet into which oxygen or other medical gas is supplied to the device, and two outlets through which oxygen or other medical gas can be selectively output from the device. The device further includes a knob or similar mechanism, e.g., partially contained in or otherwise attached to the casing, that is configured to selectively direct flow of the gas from the inlet into a selected one of the dual outlets.

In an embodiment, two and only two such outlets are provided. For example, while one may conceivably wish to include three outlets, which might potentially allow switching of the oxygen or other medical gas between three delivery devices of a given patient, there is significantly increased risk for human error where three or more such outputs are provided. For example, it is simply too easy for a practitioner to accidentally select the wrong of 3 or more outputs, meaning that the patient then receives no oxygen or other medical gas which they were intended to receive. By providing two and only two outputs, the problem of desaturation associated with time consuming switching of one mask to another mask or other device that occurs with existing delivery systems is addressed, without introducing a significant increase in the potential for human error that may have catastrophic consequences for patients.

III. Exemplary Bi-Valves

FIGS. 1-13 illustrate an exemplary bi-valve device 100. Device 100 includes a casing 102, which may be configured to include two initially separate pieces, such as an upper piece 102a and a lower piece 102b. Such initially separate pieces or "halves" may be initially separate, so as to allow positioning and assembly of the various internal components within casing 102, followed by fixing the two pieces 102a, 102b together (e.g., by adhesive or other suitable means) at joint 102c.

Figure 2:
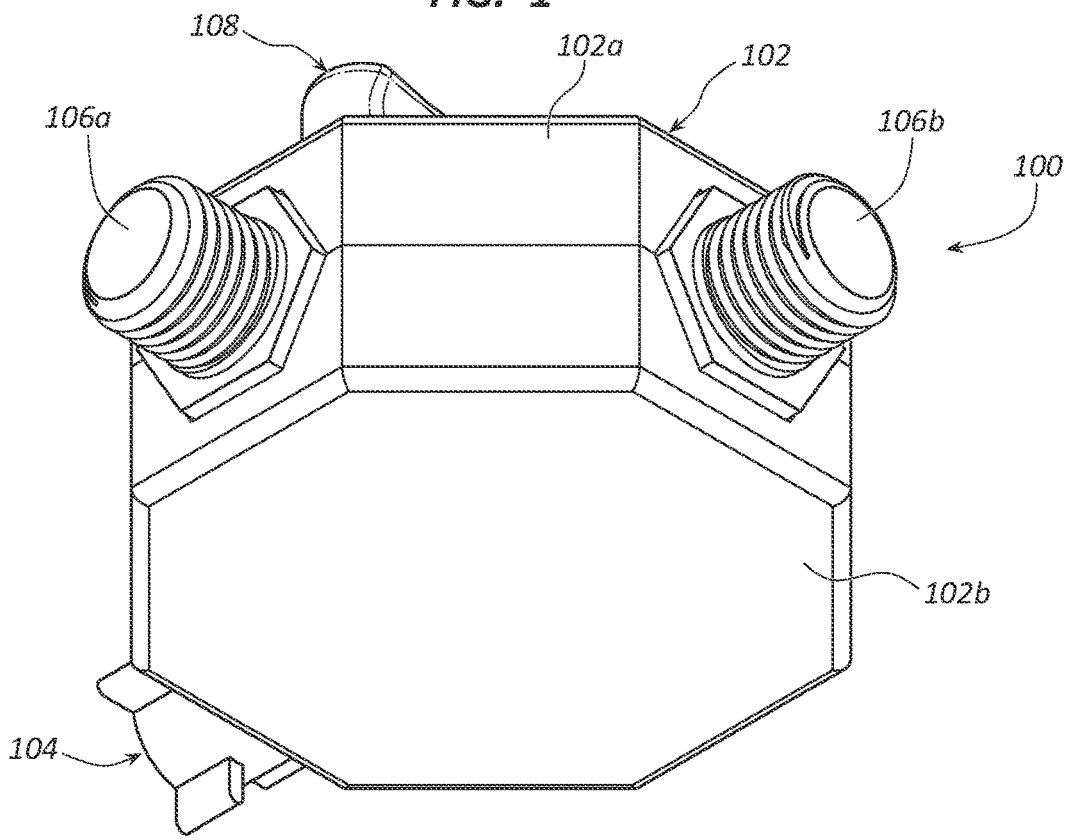
FIG. 2 is a bottom perspective view of the bi-valve device of FIG. 1.
Figure 3:
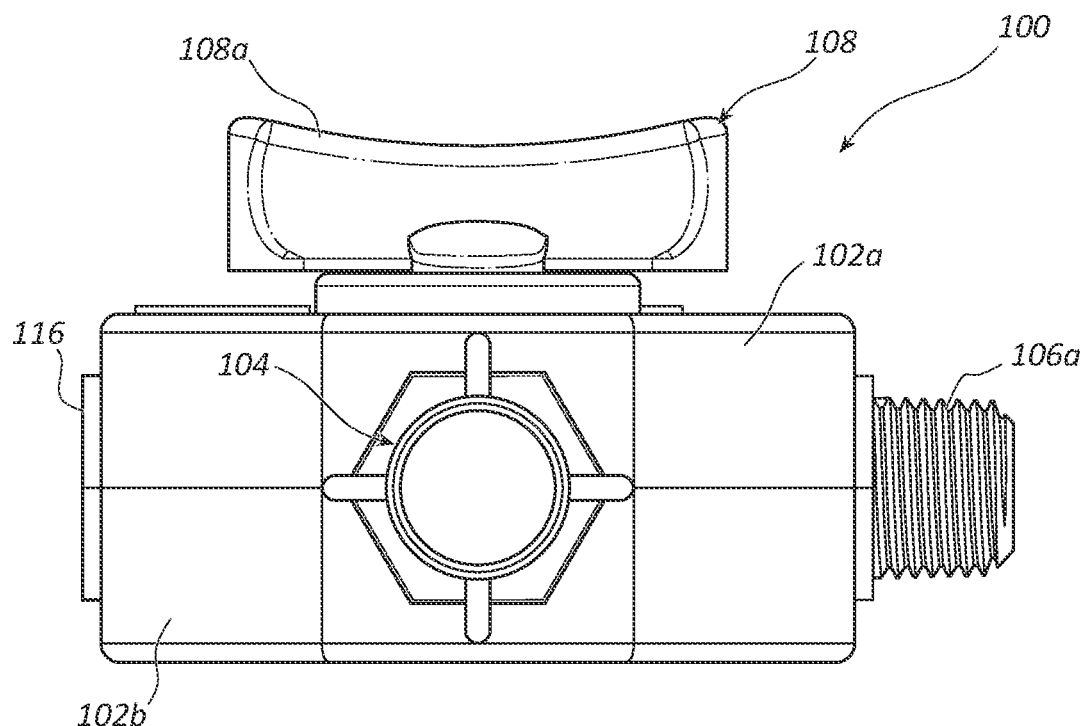
FIG. 3 is a front view of the bi-valve device of FIG. 1.
Figure 4:
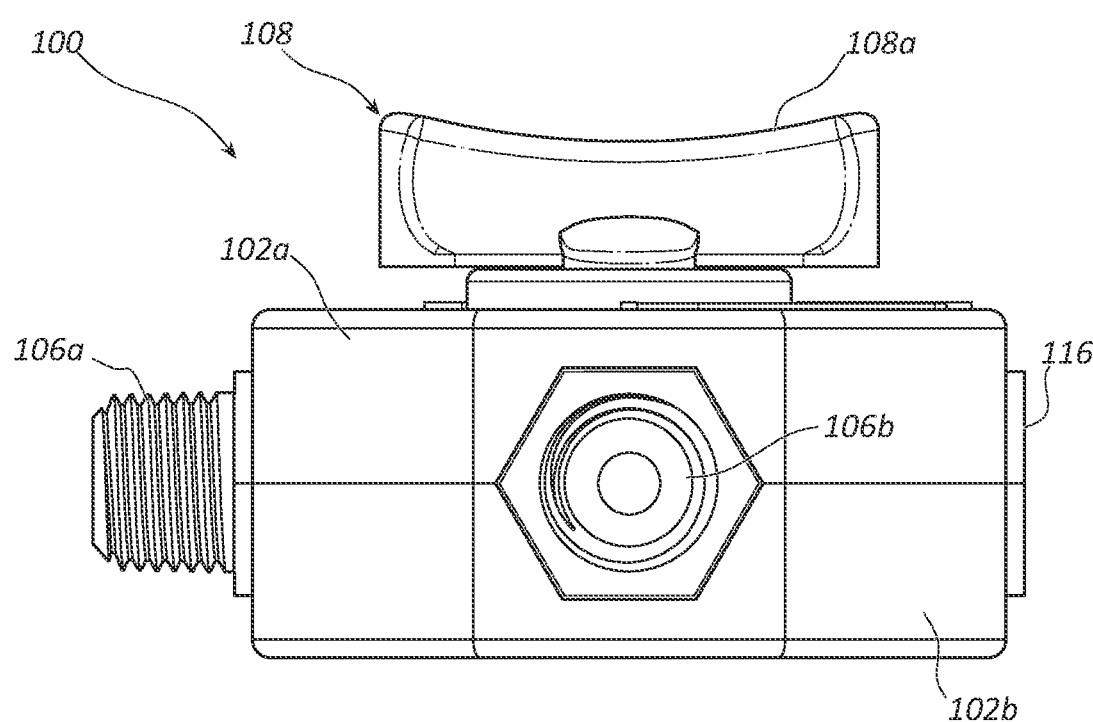
FIG. 4 is a rear view of the bi-valve device of FIG. 1.
Figure 5:
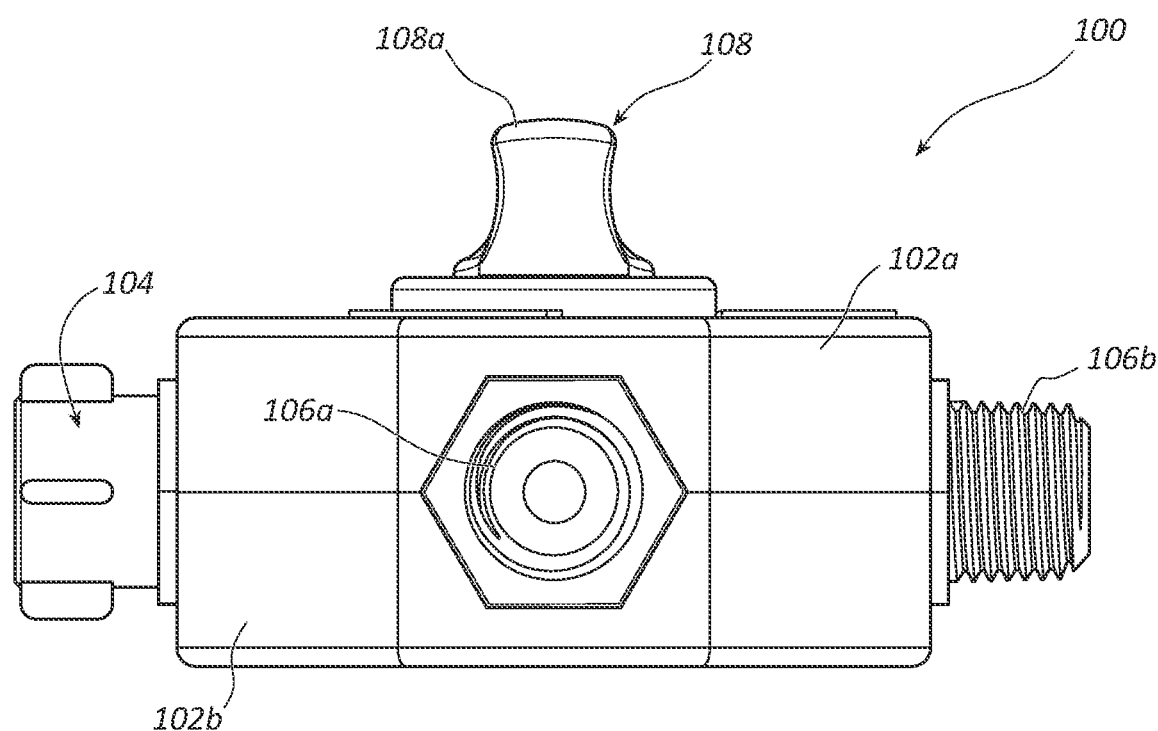
FIG. 5 is a first side view of the bi-valve device of FIG. 1.
Figure 6:
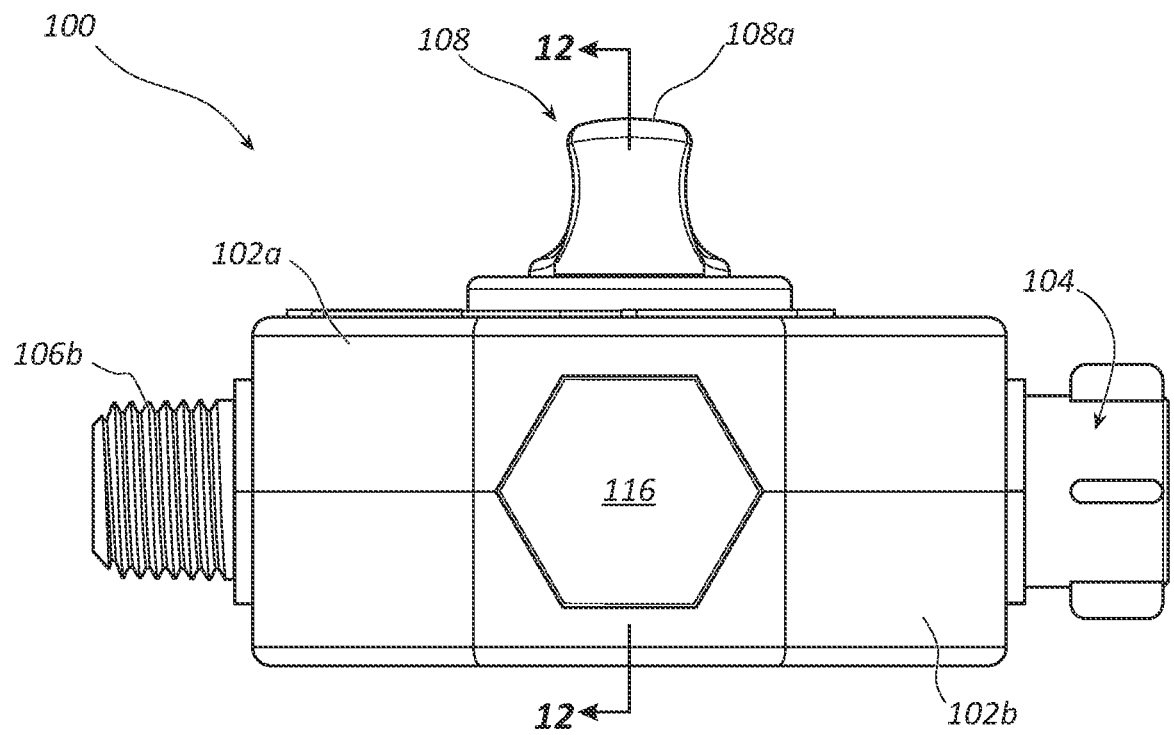
FIG. 6 is a second, opposite side view of the bi-valve device of FIG. 1.
Figure 7:
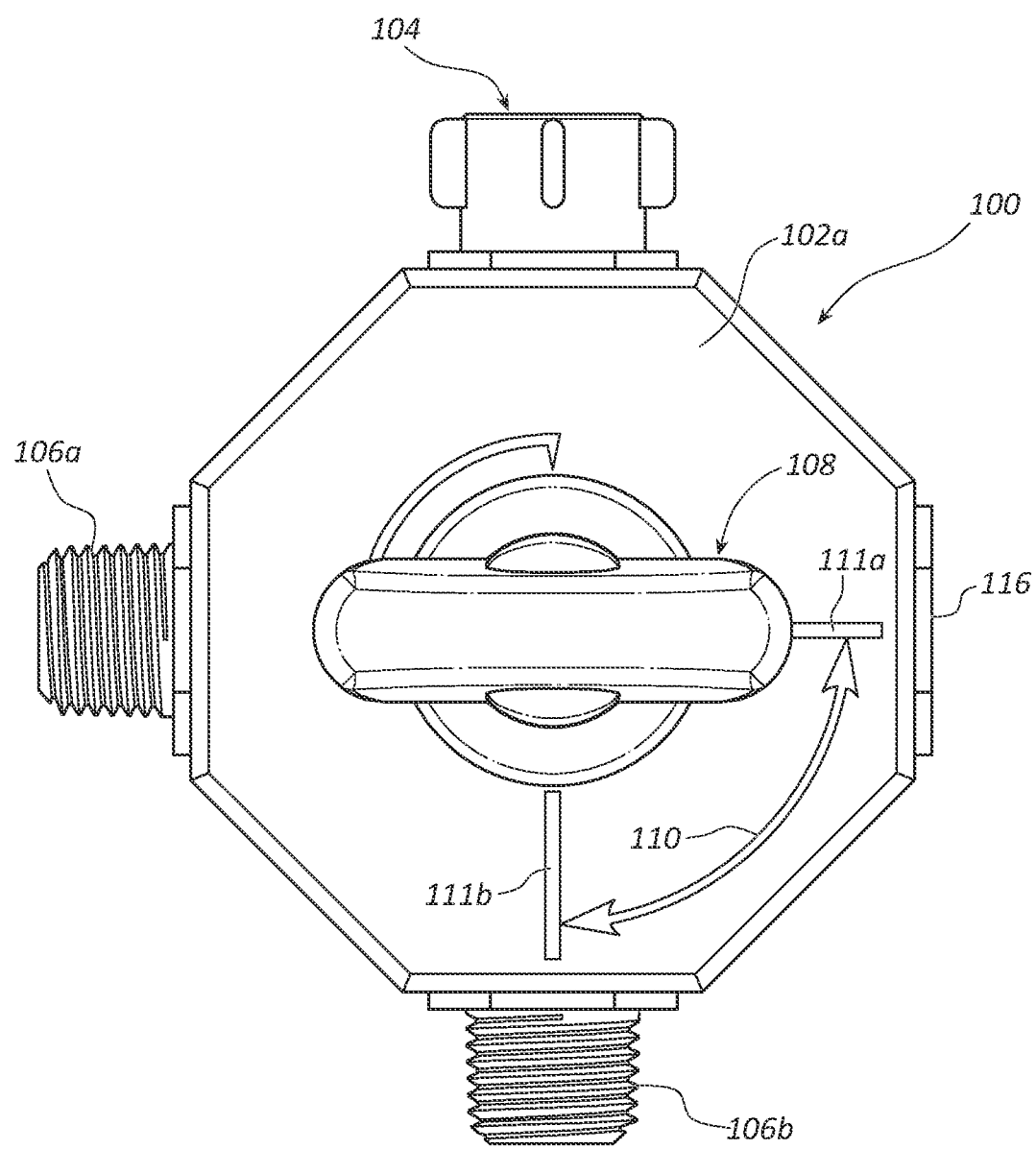
FIG. 7 is a top view of the bi-valve device of FIG. 1.
Figure 8:
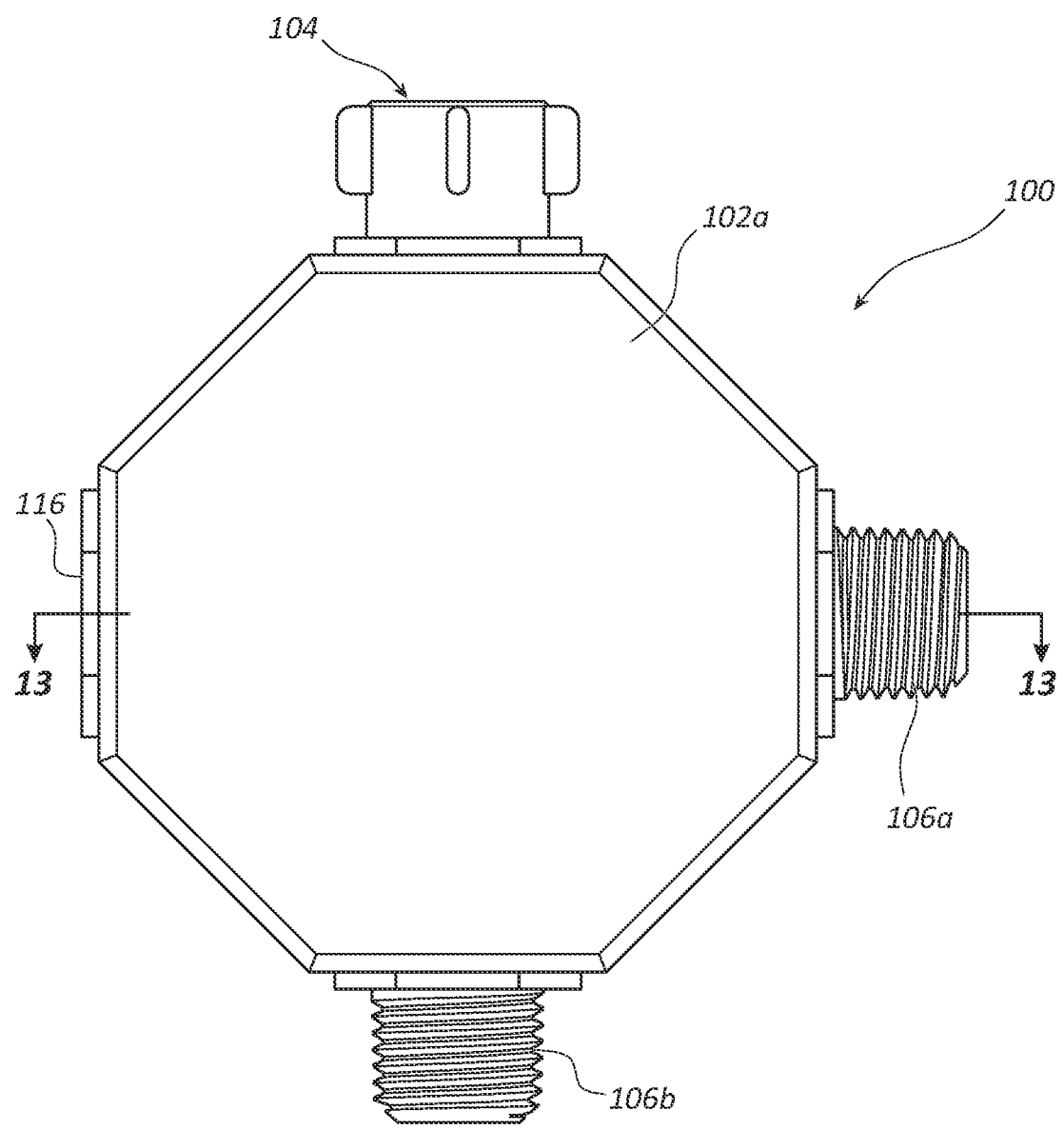
FIG. 8 is a bottom view of the bi-valve device of FIG. 1.

FIGS. 1-2 further show how device 100 includes an inlet (e.g., a single inlet) 104 and two outlets 106a and 106b. A knob 108 is shown attached to (e.g., partially contained within) the top of casing 102, e.g., above upper casing piece 102a. Knob 108 is shown as including an elongate handle portion 108a, which is easily gripped, e.g., between the thumb and index finger of a practitioner, for rotating the knob 108 between two and only two available positions. As shown, handle portion 108a may include longitudinal grooves formed into both opposing sides to facilitate easier gripping. The longitudinal ends of handle portion 108a may also provide a slight upwards slope, so as to be larger at the ends, than the middle. Such features together may aid in good hand feel, good ergonomics, minimized slippage in the hand of a user, and the like.

A first position is shown in FIG. 1, in which the longitudinal axis of handle portion 108a is aligned with (e.g., in the same plane as) first outlet 106a. Arrow 110, which may be provided on upper piece 102a of casing 102 indicates how a 90° clockwise rotation of knob 108 may result in alignment of handle portion 108a with second outlet 106b (i.e., the second position). In the first position, flow is provided from inlet 104 to first outlet 106a. In the second position, flow is provided from inlet 104 to second outlet 106b. Knob 108 may be configured to only allow for such 90° rotation, such that only those two positions (and traveling the 90° therebetween) are possible. For example, stops may be provided internally or externally to ensure that only those positions are possible. In other words, the knob 108 and other components of device 100 may be configured to not permit counter-clockwise rotation of knob 108 from the first position shown in FIG. 1. Only 90° clockwise rotation from such position to the described second position may be possible. In other words, end 109 of handle portion 108a may simply only be allowed to rotate between stop marker 111a and 111b, following the path designated by arrow 110. Such may serve as a safety feature to better ensure that the bi-valve is properly switching gas from the inlet to a single desired outlet.

Figure 9:
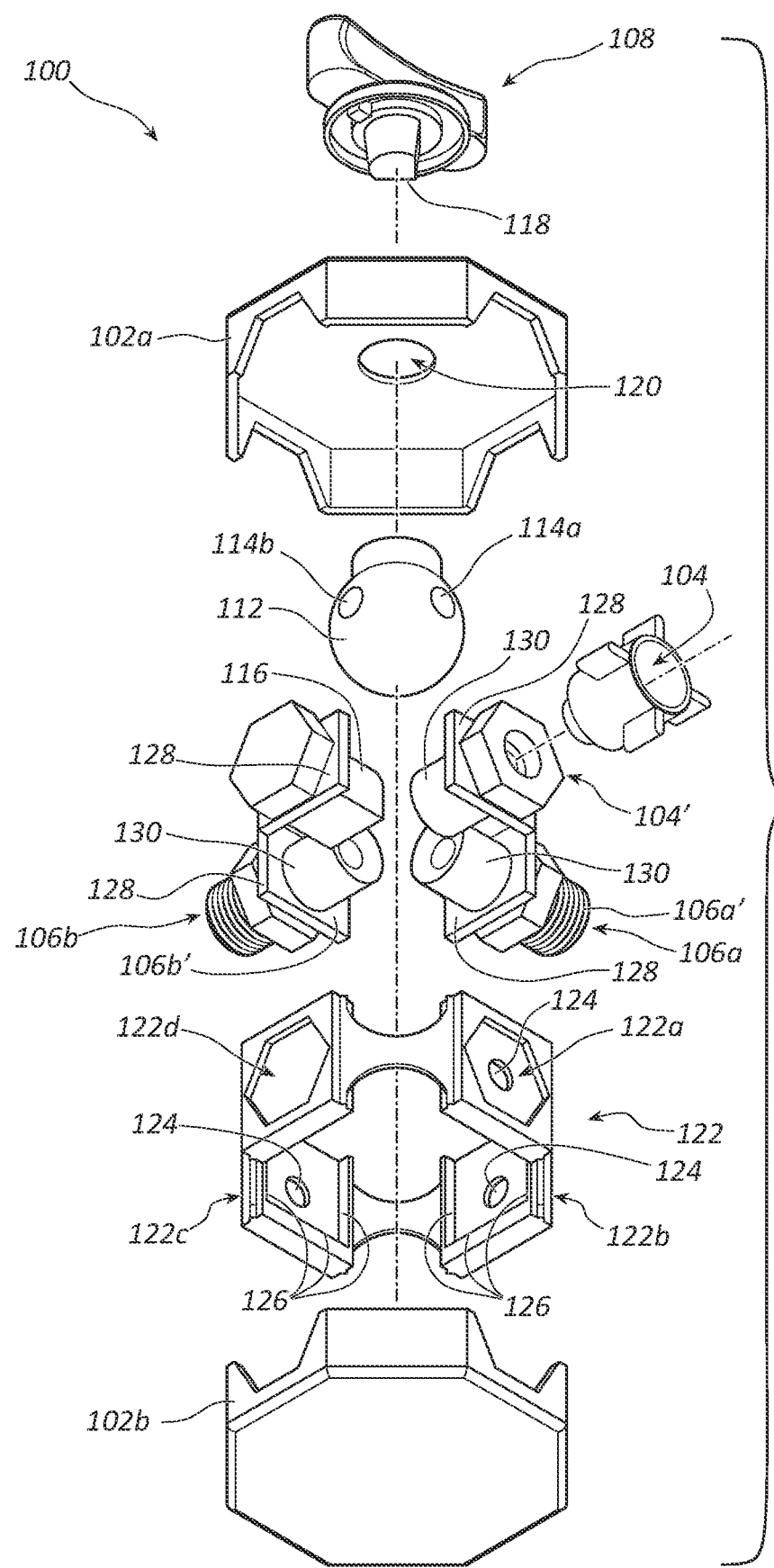
FIG. 9 is an exploded view of the bi-valve device of FIG. 1.

FIG. 9 shows an exploded view of device 100, perhaps best showing the configuration and assembly of the various components included internally. For example, as seen in FIG. 9, the device may be very simple, operating to switch from first outlet 106a to second outlet 106b by means of 3-port ball 112. As such, the device may be considered to be a ball-valve device. While FIG. 9 shows two of the ports 114a and 114b, it will be appreciated that another port 114c is also provided, e.g., 90° in a counter-clockwise direction from port 114a, e.g., so as to be aligned with first outlet 106a in FIG. 9, upon assembly of the component parts. The ports 114a, 114b and 114c thus form a "T" configuration, with ports 114b and 114c 180° apart, and port 114a in the middle, 90° from each.

As will be apparent from FIG. 9, upon assembly, port 114a is aligned with inlet 104, and unseen port 114c is aligned with first outlet 106a. Port 114b in ball 112 is aligned with a blocking member 116, which provides plugging of port 114b. This corresponds to the first position of knob 108, where flow is provided from inlet 104 to first outlet 106a. In the second position, ball 112 and all of ports 114a, 114b, and 114c rotate clockwise towards and to the second position of knob 108, such that port 114c will then be aligned with inlet 104, port 114a will be aligned with and plugged by blocking member 116, and port 114b will be aligned with second outlet 106b. In either position, one of ports 114a, 114b, or 114c is always aligned with and plugged by blocking member 116. This ensures that flow is provided only to one of the outlets 106a, 106b, depending on which is selected with knob 108.

FIG. 9 also shows how knob 108 may include a base 118 that is received into a corresponding recess in the top of ball 112. Upper casing piece 102a is also shown as including a centrally disposed hole 120 through which the base 118 passes into casing 102, for mating within the recess in ball 112. Base 118 and the corresponding recess in ball 112 may be keyed to one another. FIG. 9 shows base 118 having such a non-circular cross-section. Such a non-circular, non-symmetrical keyed feature ensures proper alignment between the knob 108 and ball 112, as base 118 can insert into the correspondingly shaped recess in ball 112 in only 1 unique and correct orientation.

FIG. 9 further shows how casing 102 may also include an internal housing 122 that may serve to receive and align and/or retain assemblies associated with the inlet 104, outlets 106a, 106b, and blocking member 116. In particular, internal housing 122 aligns or retains inlet assembly 104', outlet assemblies 106a', 106b' and blocking member 116 in their proper positions relative to one another, relative to ball 112, and relative to casing 102. For example, 3 of the 4 faces of internal housing 122 corresponding to inlet 104 (face 122a), outlet 106a (face 122b), outlet 106b (face 122c), and blocking member (face 122d) each include a hole 124, which allows flow from inlet 104 to outlets 106a, 106b, when that particular outlet is selected by knob 108 (and ball 112). Face 122d includes no such hole, as it is associated with blocking member 116, which is intended to block flow through this face of the device. Each face 122a-122d may further include an exteriorly oriented hexagonal or other shaped recess as shown to further aid in securing correspondingly shaped structure of the inlet assembly 104', the outlet assembly 106a', and the outlet assembly 106b'. Blocking member 116 may also include such correspondingly shaped hexagonal or other polygonal or other shaped structures, as well.

Internal housing 122 is also shown as including internally oriented, U-shaped, three-sided ledges 126, where the cavity defined by such ledges is open on one side (e.g., at the top), allowing insertion of a correspondingly sized and shaped insert of the inlet, outlets, or blocking member. This correspondingly sized and shaped insert of each of these 4 structures is designated 128, in FIG. 9. It will be apparent that such individually described structures of the shown assemblies 104', 106a', 106b' and 116 may be integrally formed as a single piece of material. In FIG. 9 this insert is shown as rectangular, such that it can slide down into the corresponding rectangular cavity defined by ledges 126. This configuration allows inlet assembly 104', including the illustrated tube 130 and insert 128, to slide down from above housing 122, into position, with insert 128 sliding between ledges 126, positioning the inlet assembly 104' over and aligned with face 122a, with the tube 130 aligned with hole 124. The inserts 128 of outlet assemblies 106a' and 106b' respectively, are similarly slid down into place between ledges 126 associated with faces 122b and 122c, respectively. Blocking member 116 does not include an open tube, but is closed, so as to not permit flow therethrough, but similarly slides down into place, with insert 128 thereof sliding between ledges 126 associated with face 122*d*.

The simplicity of construction and operation will be readily apparent from FIG. 9, in conjunction with the other Figures. For example, the only moving parts (which move during use and operation) may be knob 108 and ball 112. The device may not include any other moving parts, such as internal springs, discs, or the like. As such, the device is very simple to produce and use. Because of this simplicity, disposability is possible as a practical matter. For example, while any device could potentially be disposed of after a single use, or use with a single patient, many devices are complex and costly, such that as a practical matter, such is not possible. Due to the simplicity of the present device, disposability is readily achievable, as a practical matter. Such disposability decreases risk of cross-contamination from one patient to another, or even from one patient in one instance to the same patient in a different instance.

As shown in the Figures, the casing 102 may be octagon shaped. In the configuration and shape shown, 4 of the 8 octagon faces may be "blank", while the other 4 include the inlet, an outlet, or the blocking member. These 4 structures are thus spaced 90° apart from one another, with a beveled, 45° planar face between each adjacent pair of such structures. As seen in the figures, the inlet 104, outlets 106*a*, 106*b*, and blocking member 116 may be arranged so that the inlet is spaced 90° apart from first outlet 106*a*, and 180° apart from second outlet 106*b*. Blocking member 116 is positioned in one of the octagon's faces between the inlet 104 and the second outlet 106*b*. Each of the outlets 106*a*, 106*b*, and inlet 104 are all in the same plane, as shown. Such configuration is simple to use and construct. The top and bottom edges of the casing are shown as rounded, avoiding sharp edges, which can catch and be damaged. The illustrated configuration fits easily within the hand of a user, providing good ergonomics, without hand fatigue.

Figure 10:
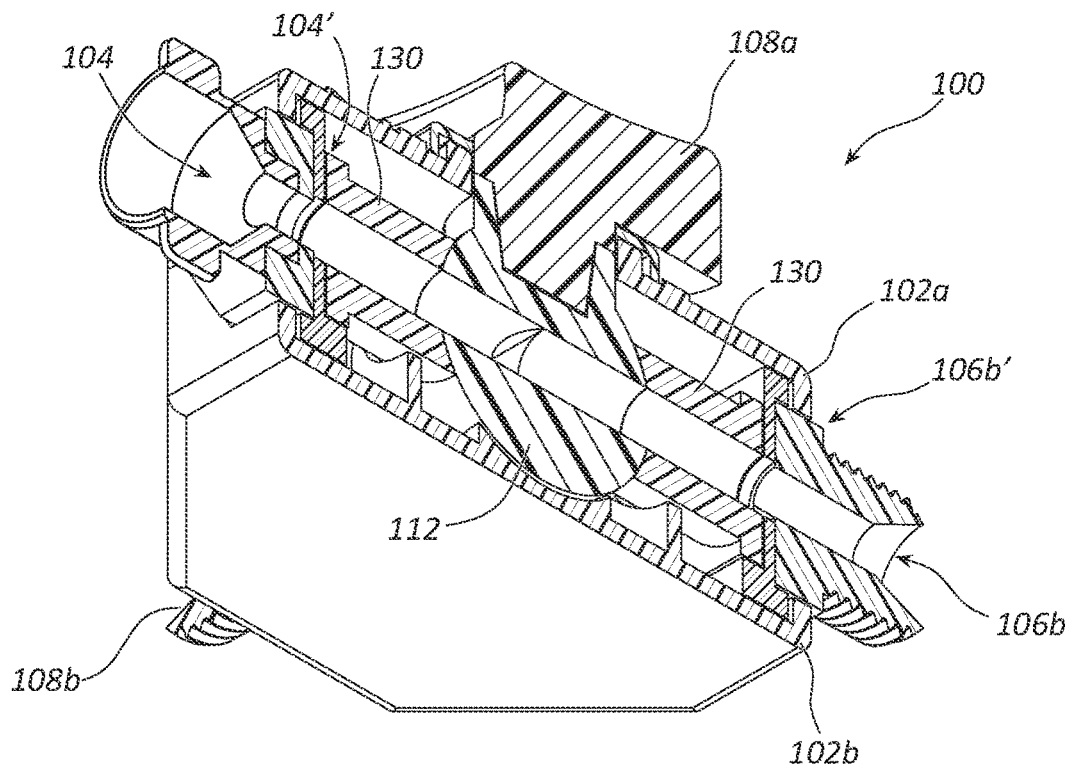
FIG. 10 is a perspective cross-sectional view through the bi-valve device of FIG. 1, taken along lines 10-10 of FIG. 1.
Figure 11:
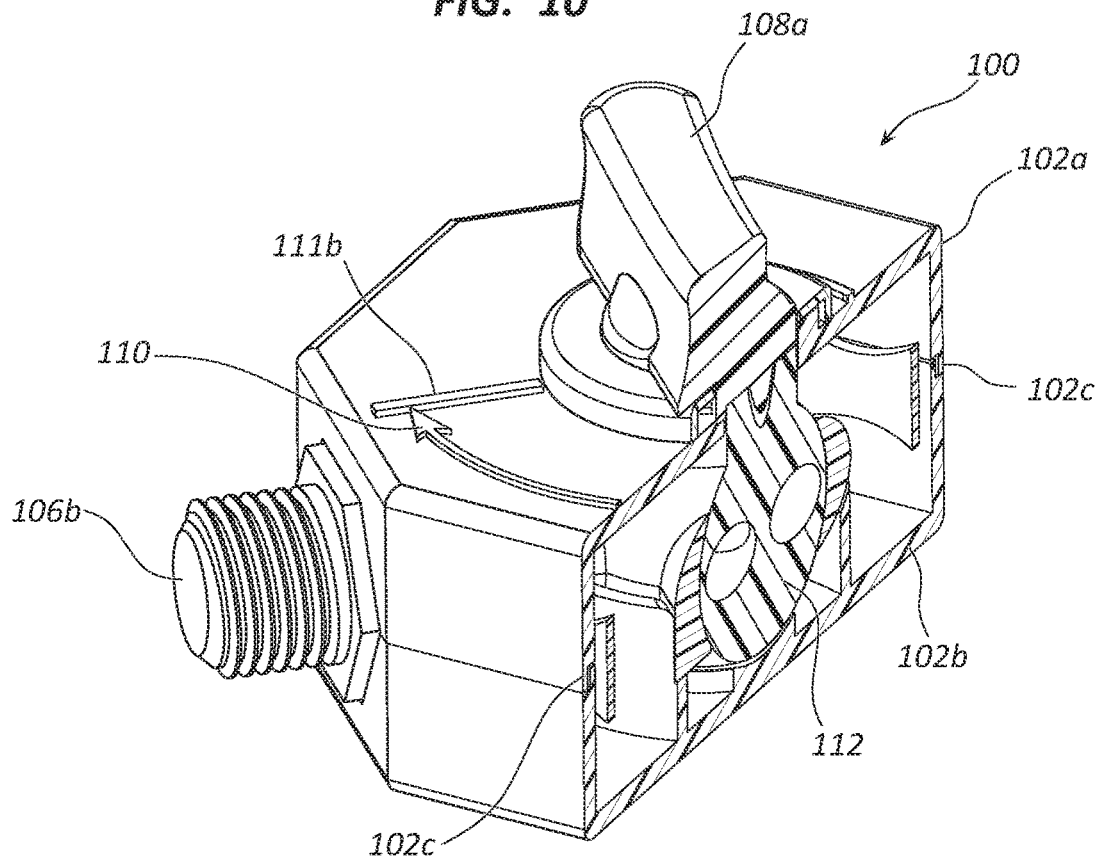
FIG. 11 is a perspective cross-sectional view through the bi-valve device of FIG. 1, taken along lines 11-11 of FIG. 1.
Figure 12:
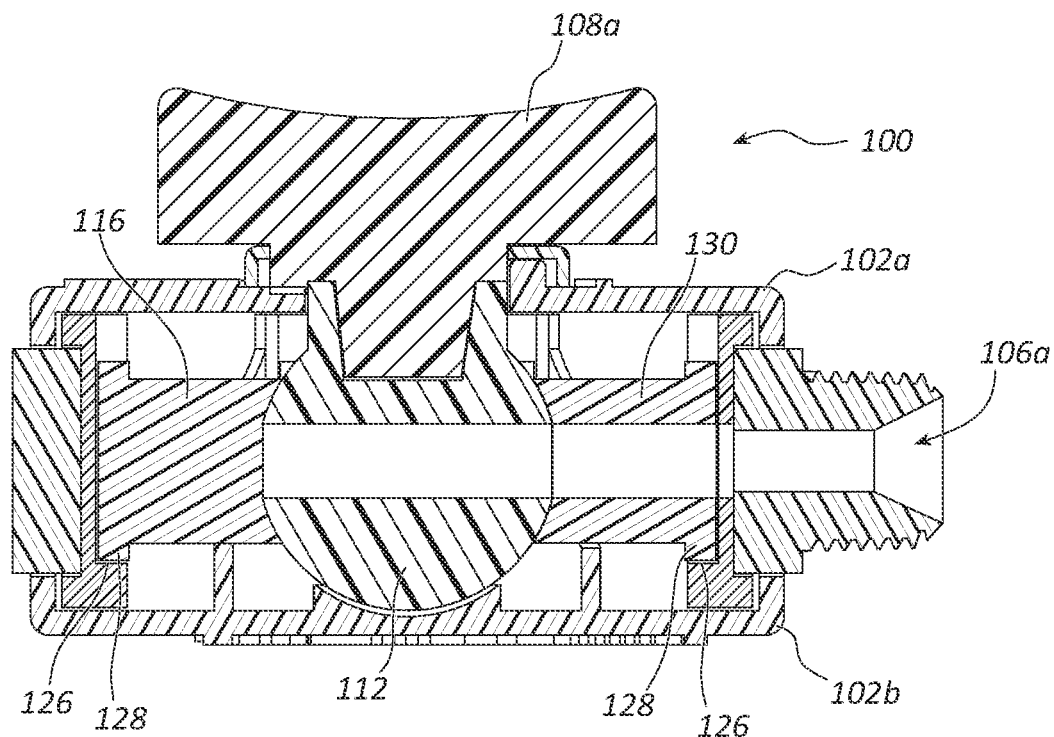
FIG. 12 is a cross-sectional view through the bi-valve device of FIG. 1, taken along lines 12-12 of FIG. 6.
Figure 13:
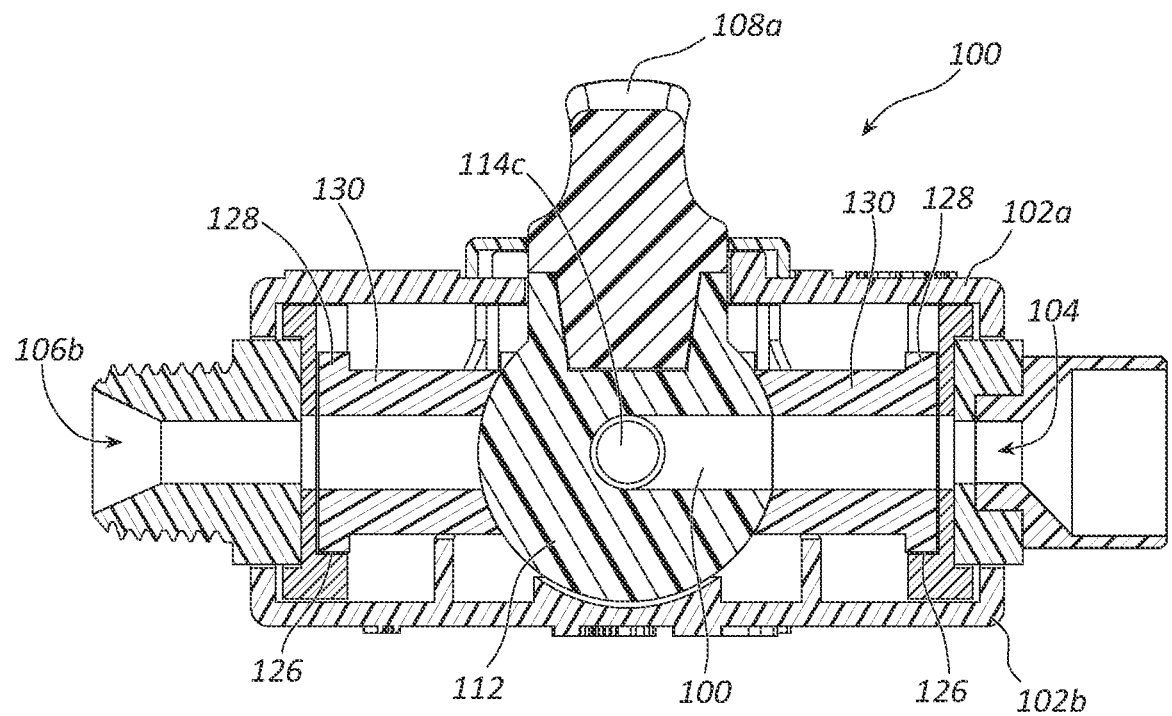
FIG. 13 is a cross-sectional view through the bi-valve device of FIG. 1, taken along lines 13-13 of FIG. 8.

FIGS. 10-13 show various cross-sectional views through device 100, clearly illustrating the fluid communication connections between the inlet 104, into ball 112, through ports 114, and a selected outlet. In particular, these views show knob 108 in the first position, aligned with first outlet 106*a*, and thus providing fluid communication between inlet 104 and first outlet 106*a*. For example, FIG. 13 shows a cross-sectional clearly showing the flow path from inlet 104 into ball 112, through port 114*a*. FIG. 12 shows the flow path from ball 112, through port 114*c* to outlet 106*a*. FIG. 10 shows a cross-section through the device, taken along the axis of the second outlet 106*b*, which is closed to flow at ball 112, due to there being no alignment between tube 130 of outlet assembly 106*b*' and ports 114*a*, 114*b*, or 114*c*. Based on the simplicity of the device, and particularly in light of FIG. 9, the flow path when knob 108 is rotated to the second position, for delivering gas to second outlet 106*b* will be readily apparent.

In an embodiment, the knob 108 may be green, e.g., which is a readily recognized color associated with medical oxygen. The remainder of the device may be white. It will be appreciated that other colors may of course be provided. All components of the device may be fabricated from inexpensive plastic and/or elastomeric materials, particularly where the device is intended to be disposable. For example, in order to provide an air-tight seal with the flow passages provided with the device, the internal tubes 130 and/or ball 112 may comprise a polymeric material capable of providing such a good seal. In some embodiments, at least some of these components may comprise an elastomeric material providing elasticity and resiliency. Other such components may comprise various suitable rigid plastic materials.

In the illustrated configuration, the outlets are shown as threaded, allowing threaded connection to a mask, cannula, or the like. It will be appreciated that numerous possible coupling configurations are possible, the illustrated threaded connections merely being exemplary.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope. Additionally, as used in this specification and the appended claims, the singular forms "a," "an" and "the" include plural referents unless the context clearly dictates otherwise.

The invention claimed is:

1. A bi-valve for use with an oxygen or other medical gas source, the bi-valve comprising:
 a casing;
 a single inlet into which oxygen or other medical gas is introduced into the casing;
 dual outlets consisting of first and second outlets through which oxygen or other medical gas can be selectively output from the casing; and
 a knob partially contained in or otherwise attached to the casing, the knob being configured to selectively direct flow of oxygen or other medical gas from the inlet into only a selected one of the first or second outlets,
 wherein the bi-valve is configured to always provide flow to only one of the first outlet or the second outlet;
 wherein the bi-valve is configured to only allow for the rotation of the knob from a first position corresponding to flow being provided to only the first outlet, to a second position corresponding to flow being provided to only the second outlet, and vice versa; and
 an internal housing within the casing, which internal housing receives an inlet assembly defining the inlet, two outlet assemblies defining the first and second outlets, and a blocking member, wherein the internal housing includes internally oriented, U-shaped, three-sided ledges, where a cavity defined by the ledges is open at a top, allowing insertion of a correspondingly sized and shaped insert comprising the inlet assembly, the outlet assemblies, or the blocking member, wherein such inserts are rectangular, such that the rectangular inserts are slidable down into a corresponding rectangular cavity defined by the ledges.

2. A bi-valve as recited in claim 1, further comprising a 3-port ball within the casing, such that the bi-valve is a ball-valve device, the 3-port ball including three ports that are spaced 90° apart from one another.

3. A bi-valve as recited in claim 1, wherein the casing is octagon shaped with 8 faces, where 4 of the 8 octagon faces are blank, and the other 4 include, respectively, the inlet, the first outlet, the second outlet, and the blocking member, where the inlet, the first outlet, the second outlet, and the blocking member are each spaced 90° apart from one another, with a beveled, 45° planar face between the inlet and the blocking member, between the blocking member and the first outlet, between the first outlet and the second outlet, and between the second outlet and the inlet, wherein each of the first outlet, the second outlet, and the inlet are all in the same plane.

4. A bi-valve as recited in claim 1, wherein the knob is partially contained within a top of the casing, the knob also extending above the casing, wherein the knob includes an elongate handle portion, the elongate handle portion including longitudinal grooves formed into opposing sides of the handle portion to facilitate easier gripping, wherein longitudinal ends of the handle portion provide an upwards slope, so as to be taller at the longitudinal ends, as compared to a middle of the handle portion, to provide at least one of improved hand feel, improved ergonomics, or minimized slippage in a hand of a user.

5. A bi-valve as recited in claim 3, further comprising a 3-port ball within the casing, such that the bi-valve is a ball-valve device, the 3-port ball including three ports that are spaced 90° apart from one another, wherein a face opposite the first outlet, between the inlet and the second outlet includes the blocking member which one of the ports of the 3-port ball aligns with and is plugged by when the knob is rotated to select oxygen or other medical gas flow to the second outlet.

6. A bi-valve as recited in claim 1, wherein the casing comprises an upper piece and a lower piece.

7. A bi-valve as recited in claim 6, wherein the knob includes a base that is received into a 3-port ball, the upper piece of the casing including a knob receiving aperture into which the base of the knob is received, such that rotation of the knob causes rotation of the 3-port ball, wherein the base of the knob is keyed to the knob receiving aperture.

8. A bi-valve as recited in claim 1, wherein the knob and a 3-port ball connected to a base of the knob are the only moving parts of the bi-valve.

9. A bi-valve as recited in claim 1, wherein the knob is an elongate knob, a longitudinal axis of the knob being aligned within the particular outlet selected for oxygen flow by the knob.

10. A bi-valve for use with an oxygen source, the bi-valve comprising:
    a two-piece casing including an upper piece and a lower piece;
    a single inlet into which oxygen is introduced into the casing;
    dual outlets consisting of first and second outlets through which oxygen can be selectively output from the casing;
    a 3-port ball disposed within the casing;
    a knob partially contained in the upper piece of the casing, the knob including an elongate rotatable handle on the upper piece of the casing and a base that is received into the 3-port ball so that the elongate rotatable handle is rotatable from (i) a first position in which oxygen flow into the inlet is directed only to the first outlet, to (ii) a second position in which oxygen flow into the inlet is directed to only the second outlet,
    wherein a longitudinal axis of the elongate rotatable handle is aligned with the first outlet when in the first position, and the longitudinal axis of the elongate rotatable handle is aligned with the second outlet when in the second position;
    wherein the bi-valve is configured to always provide flow to only one of the first outlet or the second outlet;
    wherein the bi-valve is configured to only allow for the rotation of the knob from the first position to the second position, and vice versa; and
    an internal housing within the casing, which internal housing receives an inlet assembly defining the inlet, two outlet assemblies defining the first and second outlets, and a blocking member, wherein the internal housing includes internally oriented, U-shaped, three-sided ledges, where a cavity defined by the ledges is open at a top, allowing insertion of a correspondingly sized and shaped insert comprising the inlet assembly, the outlet assemblies, or the blocking member, wherein such inserts are rectangular, such that the rectangular inserts are slidable down into a corresponding rectangular cavity defined by the ledges.

11. A bi-valve as recited in claim 10, wherein the casing is octagon shaped, and the inlet and first and second outlets are all in a single plane.

12. A bi-valve as recited in claim 10, wherein the knob and the 3-port ball are the only moving parts of the bi-valve.

13. A bi-valve as recited in claim 10, the internal housing aligning each of the inlet assembly, the two outlet assemblies, and the blocking member with the casing and the 3-port ball.

14. A method for rapidly switching oxygen or another medical gas delivered to a patient from one device to another device using a bi-valve, the method comprising:
    providing a bi-valve comprising:
        a casing;
        a single inlet into which oxygen or other medical gas is introduced into the casing;
        dual outlets consisting of first and second outlets through which oxygen or other medical gas can be selectively output from the casing; and
        a knob partially contained in or otherwise attached to the casing, the knob being configured to selectively direct flow of oxygen or other medical gas from the inlet into only a selected one of the first and second outlets,
        wherein the bi-valve is configured to always provide flow to only one of the first outlet or the second outlet;
        wherein the bi-valve is configured to only allow for the rotation of the knob from a first position corresponding to flow being provided to only the first outlet, to a second position corresponding to flow being provided to only the second outlet, and vice versa; and
        an internal housing within the casing, which internal housing receives an inlet assembly defining the inlet, two outlet assemblies defining the first and second outlets, and a blocking member, wherein the internal housing includes internally oriented, U-shaped, three-sided ledges, where a cavity defined by the ledges is open at a top, allowing insertion of a correspondingly sized and shaped insert comprising the inlet assembly, the outlet assemblies, or the blocking member, wherein such inserts are rectangular, such that the rectangular inserts are slidable down into a corresponding rectangular cavity defined by the ledges;
    attaching different devices to the first and second outlets of the bi-valve;
    rotating the knob from (i) the first position in which oxygen or another medical gas is delivered from the inlet to only the first outlet, to (ii) the second position in which oxygen or another medical gas is delivered from the inlet to only the second outlet.

15. A method as recited in claim 14, wherein the different devices attached to the first and second outlets of the bi-valve comprise a mask, cannula, bag, or nebulizer attached to the first outlet, and a different one of a mask, cannula, bag or nebulizer attached to the second outlet.

16. A method as recited in claim 14, further comprising disposing of the bi-valve after use with a single patient.

17. A method as recited in claim 14, further comprising disposing of the bi-valve after a single use.

18. A method as recited in claim 14, wherein the method is used to switch delivery of oxygen, medical grade air, nitric oxide, or heliox.

* * * * *